United States Patent
Bell et al.

(10) Patent No.: US 12,372,466 B2
(45) Date of Patent: Jul. 29, 2025

(54) METHOD FOR DETERMINING RINSE PROPERTIES

(71) Applicant: Conopco, Inc., Englewood Cliffs, NJ (US)

(72) Inventors: Fraser Ian Bell, Higher Bebington (GB); Sinead Elizabeth Bond, Liverpool (GB); Lynsey Joanne Coan, Wirral (GB); Jennifer Amy Glenday, Sheffield (GB); Raquel Gutierrez-Abad, Manchester (GB); Jun On Jamie Yip, Liverpool (GB)

(73) Assignee: Conopco, Inc., Englewood Cliffs, NJ (US)

( * ) Notice: Subject to any disclaimer, the term of this patent is extended or adjusted under 35 U.S.C. 154(b) by 263 days.

(21) Appl. No.: 17/762,571

(22) PCT Filed: Oct. 13, 2020

(86) PCT No.: PCT/EP2020/078790
§ 371 (c)(1),
(2) Date: Mar. 22, 2022

(87) PCT Pub. No.: WO2021/074156
PCT Pub. Date: Apr. 22, 2021

(65) Prior Publication Data
US 2022/0390371 A1 Dec. 8, 2022

(30) Foreign Application Priority Data
Oct. 18, 2019 (EP) ..................................... 19204110

(51) Int. Cl.
*G01N 21/64* (2006.01)
*A61K 8/81* (2006.01)
(Continued)

(52) U.S. Cl.
CPC ....... *G01N 21/6456* (2013.01); *A61K 8/8152* (2013.01); *A61Q 5/02* (2013.01);
(Continued)

(58) Field of Classification Search
CPC ....... G01N 2021/6439; G01N 21/6428; G01N 21/6456; A61Q 5/02
See application file for complete search history.

(56) References Cited

U.S. PATENT DOCUMENTS 5,928,657 A     7/1999  Simon
12,208,583 B2 * 1/2025  Andrews ................ B22F 10/68
(Continued)

FOREIGN PATENT DOCUMENTS

GB      2208297       3/1989
IN   1452/KOL/2013    12/2013
(Continued)

OTHER PUBLICATIONS

Extended European Search Report and Written Opinion on EP Patent Application No. 19204110 dated Apr. 8, 2020.
(Continued)

*Primary Examiner* — Carolyn Fin
(74) *Attorney, Agent, or Firm* — Byrne Poh LLP; Nina R. Horan

(57) ABSTRACT

A method of measuring rinse properties of a composition from a surface. The method includes providing a treatment composition comprising a UV fluorescent dye. The method also includes taking a first image of a surface. The method also includes applying the treatment composition to the surface after taking the first image. The method also includes taking a second image of the surface after applying the treatment composition to the surface. The method also includes rinsing the surface with water after taking the second image. The method also includes taking a third (Continued)

image of the surface after rinsing the surface. The method also includes analysing the first image, the second image, and the third image to quantify an amount of the treatment composition remaining on the surface after rinsing the surface.

20 Claims, 1 Drawing Sheet

(51) Int. Cl.
*A61Q 5/02* (2006.01)
*A61Q 5/12* (2006.01)
(52) U.S. Cl.
CPC ........... *A61Q 5/12* (2013.01); *G01N 21/6428* (2013.01); *G01N 2021/6439* (2013.01)

(56) References Cited

U.S. PATENT DOCUMENTS

| | | | |
|---|---|---|---|
| 2002/0037267 A1 | 3/2002 | Guillou et al. | |
| 2007/0110670 A1 | 5/2007 | Fujita et al. | |
| 2008/0303658 A1* | 12/2008 | Melker | G16H 40/20 340/540 |
| 2009/0317472 A1 | 12/2009 | Kohn et al. | |
| 2018/0344598 A1 | 12/2018 | Punyani et al. | |

FOREIGN PATENT DOCUMENTS

| | | |
|---|---|---|
| JP | H11506138 A | 6/1999 |
| JP | 2016186438 | 10/2016 |
| KR | 1020140049435 | 7/2014 |
| KR | 1020160129170 | 11/2016 |
| WO | WO97034574 | 9/1997 |
| WO | WO2005107699 | 11/2005 |
| WO | WO2012016352 | 2/2012 |
| WO | WO2013092708 | 6/2013 |
| WO | WO2014016351 | 1/2014 |
| WO | WO2014016353 | 1/2014 |
| WO | WO2014016353 A1 | 1/2014 |
| WO | WO2014016353 A4 | 1/2014 |
| WO | WO2014016354 | 1/2014 |
| WO | WO2015018853 | 2/2015 |
| WO | WO2015080521 | 6/2015 |

OTHER PUBLICATIONS

Yang et al.; Nucleic Acids Research; Determination of protein-DNA binding constants and specificities from statistical analyses of single molecules: MutS-DNA interactions; Jul. 21, 2005; pp. 4322-4334, XP055080529; vol. 33 No. 13; Oxford University Press; United States of America.
International Search Report and Written Opinion on PCT/EP2020/078790 dated Dec. 16, 2020.

* cited by examiner

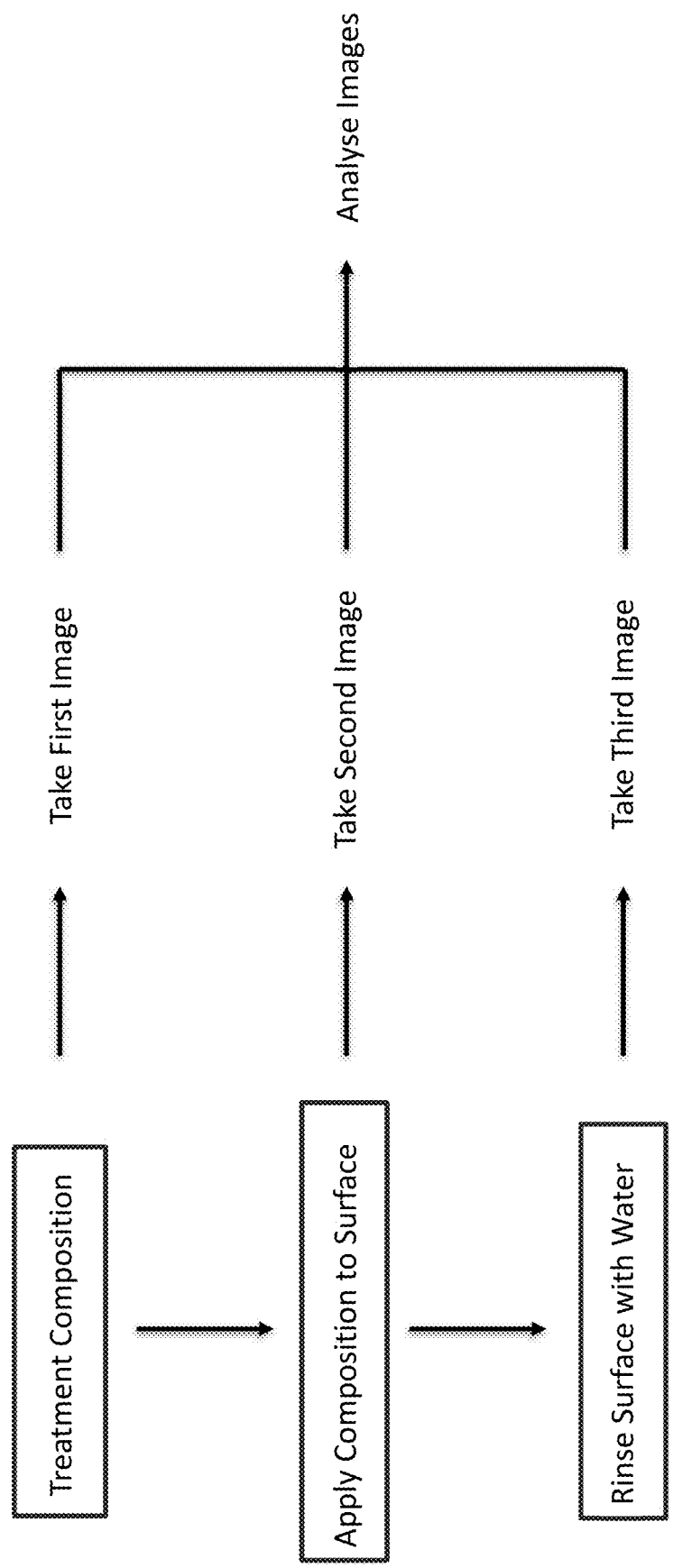

METHOD FOR DETERMINING RINSE PROPERTIES

CROSS-REFERENCE TO RELATED APPLICATIONS

This application claims priority to International Patent Application No. PCT/EP2020/078790, filed on Oct. 13, 2020, and European Patent Application No. 19204110.1, filed on Oct. 18, 2019, both of which are incorporated herein by reference in their entireties.

FIELD OF INVENTION

The present invention relates to method for determining rinse properties of compositions, having particular application in the field of hair care.

BACKGROUND AND PRIOR ART

Many products, formulated for use on surfaces, are designed to be rinsed off during use. Such products include shampoos and conditioning compositions for use on hair. These may be used as part of a hair care regime such as a daily wash and care process. These products often deposit benefit agents, for example silicones, onto the hair surface. Other, leave on, compositions deposit benefit agents onto hair that remain on the hair until the hair is next washed.

The rinsing of a composition from a surface is an important phenomenon. It can affect the way a consumer perceives product performance or makes the decision about whether to stop or continue rinsing. Rinsing properties of hair treatment compositions affect the length of time that a consumer rinses his/her hair and so directly influence, ipso facto, the amount of water that a consumer uses when using a rinse-off product.

It is known to measure the amount of foam and correlate to rinsing properties. WO 15/018853 discloses cosmetic compositions containing silicones to facilitate rinsing. Methods to measure the impact on the rinsing stage include the measurement of time needed to remove the lather, or the count of buckets or amounts of water needed. WO 05/107699 discloses foam cleansers with suspended particles. A test to determine the ability to rinse foam from hands until the foam has disappeared is described. GB 2 208 297 discloses liquid detergent compositions for laundry, household cleaning, hair and body. A rinsability test that uses measured quantities of water until no surfactant foam is seen is used.

We have, however, found that foam tracking methods have several disadvantages. Foam is sensitive to factors such as water temperature, flow rate and time. For example, foam volume can change with these variables, making such methods less accurate and difficult to reproduce. Different operators may visually assess the amount of foam differently.

IN 01452KO2013 discloses a quantitative method to measure the rinsability of cleansing formulations by measuring the conductivity of the post wash water. A formulation is applied to skin in-vivo and wash water is applied in repeated aliquots. A standard conductivity score card is then used to obtain a rinsability rating for the formulation. Despite the prior art there remains a need for a method for determining rinse properties of compositions that is accurate, reliable and accessible and that can be quickly and easily carried out.

D1: US 2009/317472 A1 discloses compositions comprising active compounds complexed with polymeric nanospheres for topical delivery through the stratum corneum. Fluorescence microscopy images of cross-sectioned human skin following topical application of actives is used to detect distribution through the skin layers.

D2: KR 2016 0129170 A discloses sunscreen compositions and a method for quantifying the cleansing effect of a cleansing composition for the sunscreen.

D3: US 2018/344598 A1 discloses hair care compositions comprising 1,2-diols and hydrophobic particles that provide durable clean feel on hair and scalp and easy sebum removal upon subsequent shampoo cleansing. UV light is used to image fluorescent dyes added to sebum that is then applied to hair before being washed with shampoo.

We have found that by using a UV fluorescent dye to enable visualization of the amount of a composition remaining on the hair surface during or after rinsing, we can provide a reliable and accessible way of predicting rinse properties of compositions, with superior accuracy. It is possible, using this method, to determine when no further composition is coming off the hair and thus to determine the end point of the rinse.

STATEMENT OF INVENTION

In a first aspect, the invention provides a method of measuring rinse properties of a composition from a surface, comprising the steps of:
  i) providing a treatment composition comprising a UV fluorescent dye;
  ii) taking a first image of the surface;
  iii) applying the composition of (i) to the surface;
  iv) taking a second image of the surface;
  v) rinsing the surface with water;
  vi) taking a third image of the surface;
  vii) analysing the images to quantify the amount of treatment composition remaining on the surface after step (v).

A preferred method includes a step of correlating the amount of treatment composition remaining on the surface after step (v) to the amount of water used to rinse the surface.

Preferably, the method includes the step of repeating steps v)-vi). Preferably at a set time interval. Preferably, the time interval is from 4 to 120 seconds, more preferably from 5 to 60 seconds, most preferably from 5 to 20 seconds.

The surface is rinsed with water. The water may be applied as a flow or as discrete quantities such as aliquots. Preferably a flow of water is used, preferably having a constant flow rate. The temperature of the water may also influence the rate of rinsing and is preferably kept constant throughout the method.

A preferred method of the invention is as follows:
  i) providing a treatment composition comprising a UV fluorescent dye;
  ii) taking a first image of the surface;
  iii) applying the composition of (i) to the surface;
  iv) taking a second image of the surface;
  v) rinsing the surface with water, which is applied as a flow at a constant flow rate and temperature;
  vi) taking a third image of the surface;
  vii) repeating steps v)-vi) at time intervals of from 5 to 60 seconds; and
  viii) analysing the images to quantify the amount of treatment composition remaining on the surface and step v).

BRIEF DESCRIPTION OF THE DRAWINGS

FIG. 1 shows a process flow diagram according to an embodiment of the disclosure.

GENERAL DESCRIPTION OF THE INVENTION

The Method

The method of the invention measures the rinse properties of a composition. The rinse properties are related to the quantity of water required to rinse the composition from a surface.

The composition is preferably a cosmetic composition. Preferably, the composition is a topical composition. A cosmetic composition, for example, a personal care composition, is intended for application to a surface, preferably the human body, particularly the skin or hair. Preferably, the surface is selected from hair and skin, most preferably, hair. Preferably the composition is selected from a hair composition (for example a hair cleansing composition, a hair conditioning composition or a hair styling composition) and a skin composition (for example, a skin cleansing composition or a skin conditioning composition).

Advantageously, the method of the invention may be used to compare rinse properties of different compositions, for example a composition before and after a modification to the composition has been carried out. This is accomplished by carrying out the method using a first treatment composition and then carrying out the method using a second treatment composition.

Preferably, the method includes repeating steps (i) to (vii) for a second treatment composition and comparing the rinse properties of the first and second treatment compositions to determine the relative rate of rinsing of the first and second treatment compositions. The composition having the greater reduction in the amount of UV dye remaining on the surface after rinsing, is rinsed faster from the surface and requires less water to be rinsed from the surface.

Preferably, the surface is wet when the images are taken. Preferably, the surface is wet when the first image is taken. The surface may be wetted with water prior to the first image being taken.

The Treatment Composition

The composition comprises a UV fluorescent dye, also referred to herein as a fluorescer.

A suitable fluorescer is a distyryl biphenyl (DSBP) type. For example, Tinopal CBS-X, available from BASF.

The composition is preferably formulated as a rinse off composition.

Preferably, the composition is structured. By structured is meant it comprises a molecular orientation that forms a gel phase or a lamellar phase.

The composition is preferably a hair treatment composition.

Rinse off hair treatment compositions for use in the present invention are preferably selected from a shampoo and a conditioner, most preferably a conditioner.

Compositions for use in the method of the invention are preferably formulated as conditioners for the treatment of hair (typically after shampooing) and subsequent rinsing.

Preferred conditioners comprise a conditioning base. The conditioning base preferably forms a gel phase.

Treatments compositions for use in the method of the current invention preferably comprise conditioning agents. Conditioning agents are preferably selected from cationic surfactants, used singly or in admixture.

Cationic surfactants useful in compositions for use in the method of the invention contain amino or quaternary ammonium hydrophilic moieties which are positively charged when dissolved in aqueous composition.

Examples of suitable cationic surfactants are those corresponding to the formula

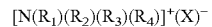

$[N(R_1)(R_2)(R_3)(R_4)]^+(X)^-$ in which $R_1$, $R_2$, $R_3$ and $R_4$ are independently selected from (a) an aliphatic group of from 1 to 22 carbon atoms, or (b) an aromatic, alkoxy, polyoxyalkylene, alkylamido, hydroxyalkyl, aryl or alklaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated. The most preferred cationic surfactants for compositions for use in the method of the present invention are monoalkyl quarternary ammonium compounds in which the akyl chain lengthy is $C_8$ to $C_{14}$.

Suitable examples of such materials correspond to the formula

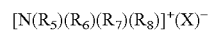

$[N(R_5)(R_6)(R_7)(R_8)]^+(X)^-$ in which $R_5$ is a hydrocarbon chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl cahins of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate and alkylsulphate radicals.

The functionalised hydrocarbyl chains (b) may suitably contain one or more hydrophilic moieties selected from alkoxy (preferably $C_1$-$C_3$ alkoxy), polyoxyalkylene, alkylester, and combinations thereof.

Preferably the hydrocarbon chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of $C_8$ to $C_{12}$ hydrocarbyl chains.

Typical monoalkyl quarternary ammonium compounds of the above general formula for use in compositions for use in the method of the invention include:

(i) Lauryl trimethylammonium chloride (available commercially as Arquad C35 ex Akzo); cocodimethyl benzyl ammonium chloride (available commercially as Arquad DMCB-80 ex-Akzo)

(ii) Compounds of the formula:

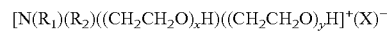

$[N(R_1)(R_2)((CH_2CH_2O)_xH)((CH_2CH_2O)_yH]^+(X)^-$ wherein:

x+y is an integer from 2 to 20;

$R_1$ is a hydrocarbyl chain having 8 to 14, preferably 12 to 14, most preferably 12 carbon atoms and containing ether, ester, amido or amino moieties present as substituent's or as linkages in the radical chain;

$R_2$ is a $C_1$-$C_3$ alkyl group or benzyl group, preferably methyl, and

X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB12 ex-Akzo Nobel); PEG-5 cocomonium methosulphate (available commercially as Rewoquat CPEM ex Rewo); PEG-15 cocomonium chloride (available commercially as Ethoquad C/25 ex-Akzo).

(iii) Compounds of the formula:

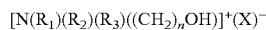

$$[N(R_1)(R_2)(R_3)((CH_2)_nOH)]^+(X)^-$$

wherein:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$-$C_3$ alkyl groups, and are preferably methyl, and X— is a salt-forming anion such as those selected from halogen, (e.g. chloride, bromide), acetate, citrate, lactate, glycolate, phosphate nitrate, sulphate, alkylsulphate radicals.

Suitable examples are lauryldimethylhydroxyethylammonium chloride (available commercially as Prapagen HY ex-Clariant).

Mixtures of any of the foregoing cationic surfactants compounds may also be suitable.

Examples of suitable cationic surfactants for use in hair compositions for use in the method of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant is cetyltrimethylammonium chloride, available commercially, for example as DEHYQUART, ex Henkel.

The level of cationic surfactant is preferably from 0.01 to 10, more preferably 0.05 to 5, most preferably 0.1 to 2 w.t. % of the total composition.

A preferred conditioner comprises a conditioning gel phase. Such conditioners and methods for making them are described in WO2014/016354, WO2014/016353, WO2012/016352 and WO2014/016351.

The conditioning compositions may also comprise other optional ingredients. Such ingredients include, but are not limited to; fatty material, deposition polymers and further conditioning agents.

Conditioner compositions preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. The level of fatty material in conditioners is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Further conditioning ingredients include esters of fatty alcohol and fatty acids, such as cetyl palmitate.

A conditioning composition for use in the present invention may preferably comprise a miscellar structured liquid.

The pH of a conditioner comprising the present composition is preferably 3-5. More preferably the pH of the composition is 4.5-5.5.

A Viscosity Reduction Agent

Preferably, the method of the invention includes a step of adding a viscosity reduction agent to the neat treatment composition to reduce the viscosity.

A preferred viscosity reduction agent is a hydrophobically modified anionic polymer Preferably, the hydrophobically modified anionic polymer is an acrylate or methacrylate polymer.

Preferably, the hydrophobic modification comprises alkylation. Preferably, the alkyl group comprises from 6 to 30 carbons, more preferably from C12 to C30, even more preferably from 16 to 28 and most preferably from 18 to 24 carbons.

A preferred polymer is sold by Rohm & Haas under the tradename Aculyn, the most preferred of which is Aculyn 28™.

The polymer is preferably added at a level of from 0.01 to 5 wt %, more preferably from 0.02 to 0 5 wt %, even more preferably from 0.03 to 4 wt % and most preferably from 0.05 to 4 wt %, by total weight of the hair treatment composition.

Preferably, the surface is a hair surface.

The UV dye is may be added to the composition in a hot phase or in a post dosing step. Preferably it is added during a hot phase to obtain a more uniform dispersion throughout the composition.

EXAMPLES

Embodiments of the invention will now be illustrated in the following examples, in which amounts are given by weight of the total composition, unless otherwise stated.

Example 1: Compositions A, B, C and D, for Use in the Method of the Invention

The following hair conditioner compositions were prepared:

Compositions A-D were hair conditioners. A and C comprise as Acrylates/Beheneth-25 Methacrylate Copolymer, which increases the rate of rinse from the surface of the hair.

TABLE 1

Compositions of conditioners A and B for use in the method of the invention

| Ingredient | A Quantity [wt %] | B Quantity [wt %] |
|---|---|---|
| Cetearyl Alcohol | 3.2 | 3.2 |
| Behenyltrimonium Chloride | 2.3 | 2.3 |
| Conditioning silicone | 1.4 | 1.4 |
| Fragrance | 0.6 | 0.6 |
| Acrylates/Beheneth-25 Methacrylate Copolymer | 0.25 | — |
| UV Fluorescer (Tinopal CBS-X ex BASF) | 0.1 | 0.1 |
| Preservative | 0.1 | 0.1 |
| water | To 100 | To 100 |

TABLE 2

Compositions of conditioners C and D for use in the method of the invention

| Ingredient | C Quantity [wt %] | D Quantity [wt %] |
|---|---|---|
| Behentrimonium Chloride | 1.4 | 1.4 |
| Cetearyl Alcohol | 3.1 | 3.1 |
| Conditioning silicone | 1.4 | 1.4 |
| Stearamidopropyl Dimethylamine | 0.3 | 0.3 |
| Fragrance | 0.6 | 0.6 |
| Acrylates/Beheneth-25 Methacrylate Copolymer | 0.500 | — |
| Lactic Acid 88% | 0.1 | 0.1 |
| Sodium Chloride | 0.1 | 0.1 |
| Preservative | 0.1 | 0.1 |
| UV Fluorescer (Tinopal CBS-X ex BASF) | 0.1 | 0.1 |
| Water | To 100 | To 100 |

The conditioners A-D were prepared using the following methods:

1. Water was added to a suitable vessel, lactic acid (if present) and copolymer (if present) were added, and the vessel heated to 80° C. The UV fluorescer was added.
2. Cetearyl alcohol was then added to the formulation along with tertiary amine salt (if present)
3. At 80° C. the Behenyltrimmonium Chloride was added (if present) and the resultant mixture mixed.
4. The heat was then turned off and quench water added.
5. The mixture was then cooled to below 40° C. and the rest of the materials were added.
6. Finally, the formulation was mixed at high shear on a Silverson mixer at 5000 rpm for 5 minutes.

Example 2: Measurement of UV Fluorescer on the Surface of Hair, Following Treatment with Compositions A-D The hair used in the following examples was dark brown European hair switches.

1. Hair switches were pre-washed with 14% SLES-1EO solution to remove any surface contamination before starting any treatment. Each switch was treated with 0.1 mL solution per g of hair and lathered for 30 s before being rinsed in warm water (35° C.-40° C., flow-rate 4 L min−1) for 30 s. The hair was combed and excess water squeezed out with the index and middle finger.
2. A first image was taken of the wet switch (image 1).
3. 2.0 g of UV conditioner A, B, C or D was applied onto the switch and spread evenly across the surface of the switch.
4. A second image was taken of the treated switch (image 2).
5. The conditioner covered switch was then placed under a flow of water (1 L/min) for the desired amount of time (in this case 5 s). At the end of the rinse time the switch was removed from the flow of water.
6. Without disrupting the surface of the switch, an image was taken (image 3).
7. Steps 5 and 6 were repeated.
8. The amount of conditioner remaining on the hair after rinsing was assessed using the following method:

The hair was placed in a UV viewing cabinet. Image analysis was performed using a suitable commercially available image analysis software, in this case, Adobe Photoshop CS5, utilising the smart grab tool to highlight the switch and the histogram tool to capture the RGB values. The higher the RGB value the brighter the switch and therefore the more conditioner present on the switch.

The results are given in the following tables:

TABLE 3

UV analysis of hair treated with Compositions A and B (Comparison of % colour change for B against A (mean +/− s.d., n = 3))

|  | Colour change at 25 s normalised | STDEV | Colour change at 30 s normalised | STDEV | Colour change at 35 s normalised | STDEV | Colour change at 40 s normalised | STDEV |
|---|---|---|---|---|---|---|---|---|
| A | 87.72 | 1.80 | 88.40 | 1.95 | 92.73 | 3.28 | 93.36 | 1.10 |
| B | 91.41 | 2.07 | 96.28 | 1.56 | 95.09 | 1.18 | 94.98 | 0.78 |

TABLE 4

Amount (% of original amount of conditioner) conditioner remaining on hair following rinsing: Conditioner B against Conditioner A (mean +/− s.d., n = 3)
Amount (%) of conditioner remaining as a function of RGB

|  | 25 s | 30 s | 35 s | 40 s |
|---|---|---|---|---|
| B | 12.28 | 11.60 | 7.27 | 6.64 |
| A | 8.59 | 3.72 | 4.91 | 5.02 |

TABLE 5

Results of the Tukey Kramer multiple comparison test.

| Composition | Connecting letter | | |
|---|---|---|---|
| A - 30 s | A | | |
| A - 35 s | A | B | |
| A - 40 s | A | B | |
| B - 40 s | A | B | C |
| B - 35 s | | B | C |

TABLE 6

UV analysis of hair treated with Compositions C and D (Comparison of % colour change for D against C (mean +/− s.d., n = 3))

| | Colour change at 20 s normalised | STDEV | Colour change at 25 s normalised | STDEV | Colour change at 30 s normalised | STDEV |
|---|---|---|---|---|---|---|
| D | 79.27 | 4.24 | 80.98 | 9.19 | 99.14 | 1.34 |
| C | 88.09 | 1.79 | 93.85 | 1.18 | 99.55 | 0.47 |

TABLE 7

Table 4: Amount (% of original amount of conditioner) conditioner remaining on hair following rinsing: Conditioner D against Conditioner C (mean +/− s.d., n = 3)
Amount (%) of conditioner remaining as a function of RGB

| | 20 s | 25 s | 30 s |
|---|---|---|---|
| D | 20.73 | 19.02 | 0.86 |
| C | 11.91 | 6.15 | 0.45 |

TABLE 8

Results of the Tukey Kramer multiple comparison test.

| Composition | Connecting letter | | |
|---|---|---|---|
| C - 30 s | A | | |
| D - 30 s | A | | |
| C - 25 s | A | B | |
| C - 20 s | | B | C |
| D - 25 s | | | C |
| D - 20 s | | | C |

In conclusion the method of the invention enables rinse properties to be measured accurately for different types of composition.

What is claimed is:

1. A method of measuring rinse properties of a composition from a surface, the method comprising:
   providing a treatment composition comprising a UV fluorescent dye;
   taking a first image of the surface;
   applying the treatment composition to the surface after taking the first image;
   taking a second image of the surface after applying the treatment composition to the surface;
   rinsing the surface with water after taking the second image;
   taking a third image of the surface after rinsing the surface; and
   measuring an amount of the treatment composition remaining on the surface after rinsing the surface by capturing red green blue (RGB) values from the first image, the second image, and the third image, wherein an increase in the RGB value corresponds to an increase in the amount of the treatment composition remaining on the surface.

2. The method of claim 1, further comprising:
   rinsing the surface with water after taking the third image; and
   taking a fourth image of the surface after rinsing the surface after taking the third.

3. The method of claim 2, further comprising waiting a time between 4 seconds and 120 seconds after taking the third image before rinsing the surface.

4. The method of claim 1, wherein the water is a flow of water.

5. The method of claim 1, further comprising correlating an amount of the treatment composition remaining on the surface after rinsing the surface to an amount of the water used to rinse the surface.

6. The method of claim 1, wherein the first image is taken when the surface is wet.

7. The method of claim 1, wherein the surface is hair or skin.

8. The method of claim 7, wherein the surface is hair.

9. The method of claim 1, wherein the treatment composition is a cosmetic composition.

10. The method of claim 9, wherein the composition is a structured composition that comprises a molecular orientation that forms a gel phase or a lamellar phase.

11. The method of claim 1, further comprising:
   providing a second treatment composition;
   taking a fourth image of the surface;
   applying the second treatment composition to the surface after taking the fourth image;
   taking a fifth image of the surface after applying the second treatment composition to the surface;
   rinsing the surface with water after taking the fifth image;
   taking a sixth image of the surface after rinsing the surface after taking the fifth image;
   measuring a second amount of the second treatment composition remaining on the surface after rinsing the surface, by capturing RGB values from the fourth image, the fifth image, and the sixth image, wherein an increase in the RGB value corresponds to an increase in the second amount of the second treatment composition remaining on the surface; and
   comparing rinse properties of the treatment composition and the second treatment composition to determine relative rate of rinsing of the treatment composition and the second treatment composition.

12. A method comprising:
   rinsing a first surface;
   taking a first image of the first surface after rinsing the first surface;
   applying a first treatment composition to the first surface after taking the first image;
   taking a second image of the first surface after applying the first treatment composition;

rinsing the first surface after taking the second image;
taking a third image of the first surface after rinsing the first surface; and
measuring a first amount of the first treatment composition remaining on the first surface, by capturing red green blue (RGB) values from the first image, the second image, and the third image, wherein an increase in the RGB value corresponds to an increase in the first amount of the first treatment composition remaining on the first surface.

13. The method of claim 12, further comprising:
rinsing a second surface;
taking a fourth image of the second surface after rinsing the second surface;
applying a second treatment composition to the second surface after taking the fourth image;
taking a fifth image of the second surface after applying the second treatment composition;
rinsing the second surface after taking the fifth image;
taking a sixth image of the second surface after rinsing the second surface; and
measuring a second amount of the second treatment composition remaining on the second surface, by capturing RGB values from the fourth image, the fifth image, and the sixth image, wherein an increase in the RGB value corresponds to an increase in the second amount of the second treatment composition remaining on the second surface.

14. The method of claim 13, further comprising comparing the first amount and the second amount to determine a relative rate of rinsing of the first treatment composition and the second treatment composition.

15. The method of claim 13, wherein:
the first treatment composition is a fluorescer; and
the second treatment composition is a fluorescer.

16. The method of claim 13, wherein:
the first treatment composition is configured to form a gel phase or a lamellar phase; and
the second treatment composition is configured to form a gel phase or a lamellar phase.

17. The method of claim 13, wherein:
the first treatment composition is a shampoo or a conditioner; and
the second treatment composition is a shampoo or a conditioner.

18. The method of claim 13, wherein:
the first treatment composition comprises an ultraviolet dye; and
the second treatment composition comprises an ultraviolet dye.

19. The method of claim 13, further comprising:
placing the first surface in an ultraviolet viewing cabinet after rinsing the first surface and prior to taking the third image; and
placing the second surface in the ultraviolet viewing cabinet after rinsing the second surface and prior to taking the sixth image.

20. The method of claim 13, wherein:
measuring the first amount comprises comparing first red green blue (RGB) values of the first image, second RGB values of the second image, and third RGB values of the third image; and
measuring the second amount comprises comparing fourth RGB values of the fourth image, fifth RGB values of the fifth image, and sixth RGB values of the sixth image.

* * * * *